United States Patent [19]

Kaster

[11] Patent Number: 4,488,318
[45] Date of Patent: Dec. 18, 1984

[54] PROSTHETIC HEART VALVE

[76] Inventor: Robert L. Kaster, 2730 Vagabond La., Plymouth, Minn. 55447

[21] Appl. No.: 366,150

[22] Filed: Apr. 7, 1982

[51] Int. Cl.³ .................. A61F 1/22; F16K 15/03
[52] U.S. Cl. .................. 3/1.5; 137/512.1; 137/527
[58] Field of Search .......... 3/1.5; 137/512, 512.1, 137/527, 527.8

[56] References Cited

U.S. PATENT DOCUMENTS

| Re. 30,507 | 2/1981 | Kaster | 3/1.5 |
|---|---|---|---|
| 3,113,586 | 12/1963 | Edmark, Jr. | 3/1.5 X |
| 3,416,562 | 12/1968 | Freeman | 3/1.5 X |
| 3,513,485 | 5/1970 | Davila | 3/1.5 |
| 3,589,392 | 6/1971 | Meyer | 3/1.5 X |
| 4,021,863 | 5/1977 | Woien | 3/1.5 |
| 4,030,142 | 6/1977 | Wolfe | 3/1.5 |
| 4,178,638 | 12/1979 | Meyer | 3/1.5 |
| 4,254,508 | 3/1981 | Bokros | 3/1.5 |
| 4,291,419 | 9/1981 | Intonti et al. | 3/1.5 |
| 4,306,319 | 12/1981 | Kaster | 3/1.5 |
| 4,308,624 | 1/1982 | Klawatter | 3/1.5 |
| 4,328,592 | 5/1982 | Klawitter | 3/1.5 |

Primary Examiner—Ronald L. Frinks
Attorney, Agent, or Firm—Merchant, Gould, Smith, Edell, Welter & Schmidt

[57] ABSTRACT

An improved check valve which is particularly adapted for surgical implantation in the heart as a substitute for a natural heart valve. In one embodiment, the prosthetic valve (10) comprises a circular base (40) on which a pair of semiconical leaflets (42) are supported for pivotal movement between open and closed positions by T-shaped arms (60) and pin and slot connections. In a second embodiment (80), the semiconical leaflets (42′) are supported and constrained for pivotal movement between open and closed positions by C-shaped arms (82) engaging apertures (84) and notches (86) on the leaflets. In the preferred construction, at least one of the leaflets (42, 42′) can also translate for ease of operation.

14 Claims, 12 Drawing Figures

PROSTHETIC HEART VALVE

TECHNICAL FIELD

The present invention relates generally to check valves, and particularly to a prosthetic heart valve having semiconical leaflets asymmetrically hinged within an annular base for movement between open and closed positions to control directional flow of blood through the heart.

BACKGROUND ART

The heart includes four natural valves that function to regulate flow direction as blood is pumped between the lungs and various blood vessels comprising the circulatory system of the body. Pumping of the blood is primarily carried out by contraction and expansion of the ventricles, the lowermost heart chambers.

The mitral and tricuspid valves interconnect the left and right atria, respectively, and their corresponding ventricles. Flow is from the atrium to the ventricle. When the ventricle contracts, the resulting pressure differential closes the valve between the chambers so that blood is forced outwardly from the heart. When the ventricle relaxes, the reduction in intraventricular pressure to a lesser level than the atrial pressure causes the valve to open and blood to flow from the atrium into the ventricle. The mitral and tricuspid valves, which are known as the atrioventricular or intraflow valves, thus operate to prevent backflow into the atria during ventricular contraction while permitting blood to flow therethrough during ventricular relaxation.

The aortic and pulmonary valves, on the other hand, are known as semilunar or outflow valves and are located where blood leaves the heart. The aortic valve interconnects the left ventricle with the aorta, while the pulmonary valve is located at the junction between the right ventricle and pulmonary artery.

A relatively common human ailment is failure of one or more valves of the heart. In many cases, the diseased or defective valve can be surgically removed and replaced with a prosthetic valve, thereby improving the life of the patient. Although serious, such valve replacement surgery has become commonplace in recent years.

Various prosthetic heart valves have been developed for this purpose. Such valves can be grouped into three general types with each prosthetic valve including either a ball, disc or leaflet type flow regulating device supported by a valve housing that is fixed in place by means of suturing between the natural valve annulus and the prosthetic valve sewing ring. For example, U.S. Pat. No. 3,589,392 to Meyer shows a valve of the split leaflet type wherein the separable leaflet portions are generally arcuate in cross section and are tethered or hinged at their bases to the valve body in a symmetric manner by means of an insertable ring member. U.S. Pat. No. 4,254,508 to Bokros discloses a bileaflet heart valve wherein flat leaflets are pivotally supported by means of pin and slot connections. The heart valve prosthesis of U.S. Pat. No. Re. 30,507 to Kaster and that of U.S. Pat. No. 4,021,863 to Woien utilize free-floating pivoting circular discs that can also rotate, while the valve in U.S. Pat. No. 4,306,319 to Kaster incorporates a pivoting non-circular disc that cannot rotate. U.S. Pat. No. 3,113,586 to Edmark shows a valve of the flexible leaflet type. U.S. Pat. Nos. 4,030,142 to Wolfe and 3,513,485 to Davila relate to prosthetic heart valves utilizing movable occluder elements that are centrally supported within a housing ring or base.

Of course a prosthetic heart valve must be compatible with and acceptable by the heart and blood; however, various difficulties can arise due to deficiencies in design, operational characteristics, physical structure, and structural materials. Some of the prior designs have been functionally inefficient, unresponsive and resistive of the free passage of blood. Others cause blood stagnation and turbulence that results in the formation of blood clots on the valve structure that impede the normal valving movements of the prosthesis. Elevated levels of hemolysis (destruction of red blood cells) can occur in some valves that have rough surfaces and/or small or narrow flow passages. Hemolysis also can occur in valves having hard and substantial contact surface areas or interfaces such as between a stationary valve member and a mobile valve member or occluder. In such valves, blood cells become trapped between these surfaces and are mechanically crushed thus reducing their useful life span.

The operational characteristics of some early prosthetic valves cause elevated transvalvular pressure gradients, diminished stroke volume and record small functional or effective orifice areas. Blood flow through the natural healthy valve(s) is directed centrally downstream; however, blood flow through a caged-ball or caged-disc valve is directed radially from the center of the valve by the respective occluder. The subsequently developed pivoting disc valves permit the blood to flow nearly centrally downstream but deflected from the central axis an amount equal to the design angle of the disc occluder in the open position. Improvement in valvular hemodynamic efficiency continues to be made but no prosthetic valve functions as efficiently as the normal healthy cardiac valve(s).

Although the earlier developed caged-ball concept is generally recognized as a predictable prosthesis, it is also known to be an excessively bulky valve due to its relatively large physical cage structure. In some patients implanted with a caged-ball valve where there is limited space for such bulky valve structures, the extending cage can engage the internal wall surface of heart and disrupt the natural beating and pumping rhythm which in turn can frequently cause cardiac arrest. The lower profile disc valves represent a reduction in physical structure and bulk and thus do not involve some of the problems associated with cage-ball valves.

With respect to materials, except for the supporting struts of some tissue valves and the sewing ring of most all valves, plastics have not been found to perform satisfactorily. Silicone rubber when used in the construction of the ball of some caged-ball valves or the disc of some caged-disc valves have been known to deteriorate due to wear and chemical degradation. Other plastic materials, such as TEFLON, DELRIN, LUCITE, polypropylene and others have recorded equally disappointing results in prosthetic heart valves of various designs.

A need thus exists for a new prosthetic heart valve of improved design, performance and construction over the prior art.

SUMMARY OF THE INVENTION

The present invention comprises a check valve, particularly adapted for implantation as a prosthetic heart valve, that overcomes the foregoing and other difficulties associated with the prior art. In accordance with the invention, there is provided an artificial heart valve comprising a pair of semiconical leaflets supported for movement between open and closed positions by a circular base or housing adapted for receiving a sewing ring by which the valve can be sutured in place. The semiconical leaflets are asymmetrically supported such that one leaflet can translate slightly longitudinally downstream relative to the other leaflet to facilitate opening and closing. In one embodiment, the leaflets are supported by T-shaped members extending from the base and which engage slots formed in brackets on the downstream sides of the leaflets. In another embodiment, the leaflets are supported by C-shaped retaining-/control struts extending from the base which project through slots and notches formed directly in the leaflets. Prosthetic valve sewing rings are known to the art and although a sewing ring is important to the proper surgical implantation of this and most other heart valves, no particular sewing ring is essential to ensure the correct valving operation of the valve of this invention.

BRIEF DESCRIPTION OF DRAWINGS

A better understanding of the invention can be had by reference to the following Detailed Description in conjunction with the accompanying Drawings, wherein.

DETAILED DESCRIPTION

Figure 1:
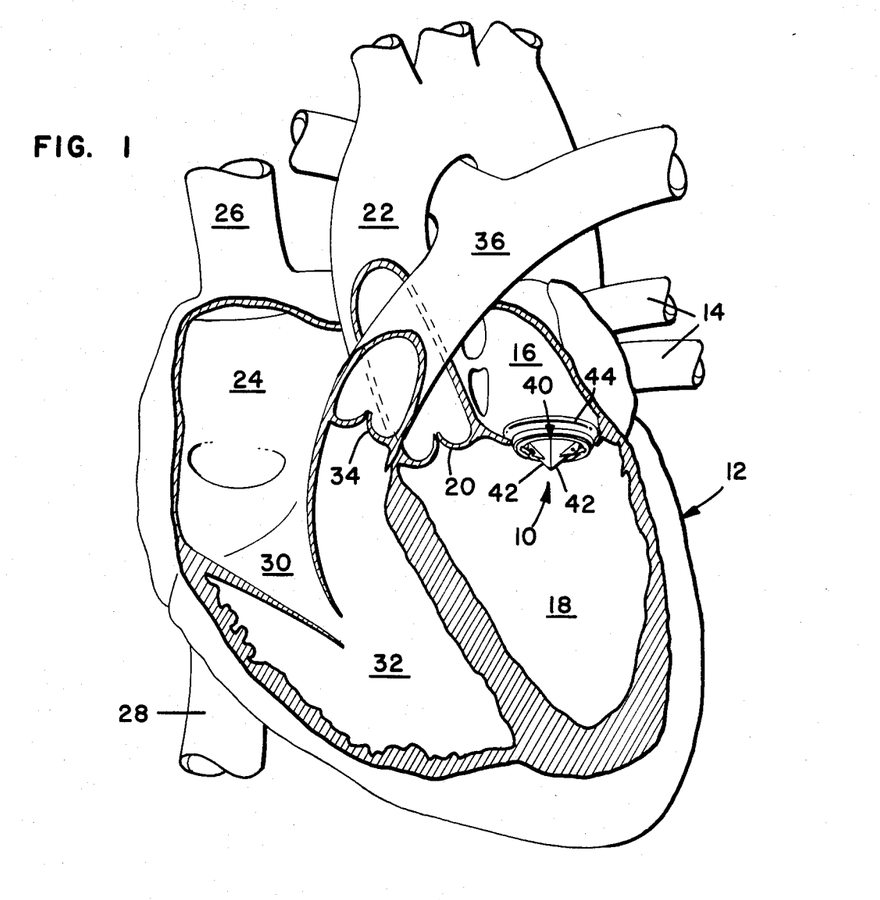
FIG. 1 is a perspective view of a heart (partially cut away) with the prosthetic valve of the invention and surrounding sewing ring mounted in the mitral position.

Referring now to the Drawings, wherein like reference numerals designate like or corresponding elements throughout the views, and particularly referring to FIG. 1, there is shown a valve 10 incorporating the invention mounted in the mitral position within a heart 12. Briefly, the interior of the heart is divided into four chambers and includes four valves that control the direction of blood flow therethrough. Oxygenated blood from the lungs (not shown) is conducted by the pulmonary veins 14 into the left atrium 16, from which it flows through the prosthetic mitral valve 10 into the left ventricle 18, and is then pumped through the natural aortic valve 20 into the aorta 22 and on through the arterial system in the body. After circulating through the tissues of the body, blood enters the venous system and returns to the heart 12 where it enters the right atrium 24 from the superior vena cava 26 and inferior vena cava 28. The blood received in the right atrium 24 flows through the natural tricuspid valve 30 into the right ventricle 32 and is then pumped through the natural pulmonary valve 34 into the pulmonary artery 36 and back to the lungs for reoxygenation.

Although the prosthetic valve 10 is shown in the mitral position, it will be appreciated that it can be used as a prosthesis for any one of the four natural valves in heart 12, although the pulmonary valve 34 is rarely replaced by direct implantation at the natural valve site. Instead, the prosthetic valve 10 would typically be attached to a fabric tube graft (not shown) which is sutured in place between the natural pulmonary valve annulus and pulmonary artery 36. Prosthetic heart valves, however, are most often employed in the mitral or aortic positions, and valve 10 is especially well suited for use at either of these sites.

While the valve 10 described and illustrated herein is particularly suited for use as a prosthetic heart valve, it will be understood that the valve is essentially a check valve and thus can easily be adapted for use in other flow control applications.

Figure 2:
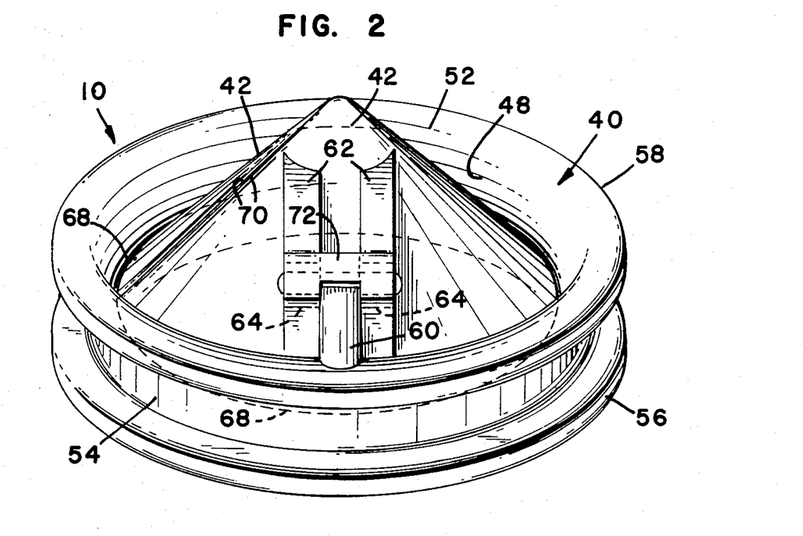
FIG. 2 is an enlarged perspective view from the outflow aspect of a first embodiment of the invention without the sewing ring.
Figure 3:
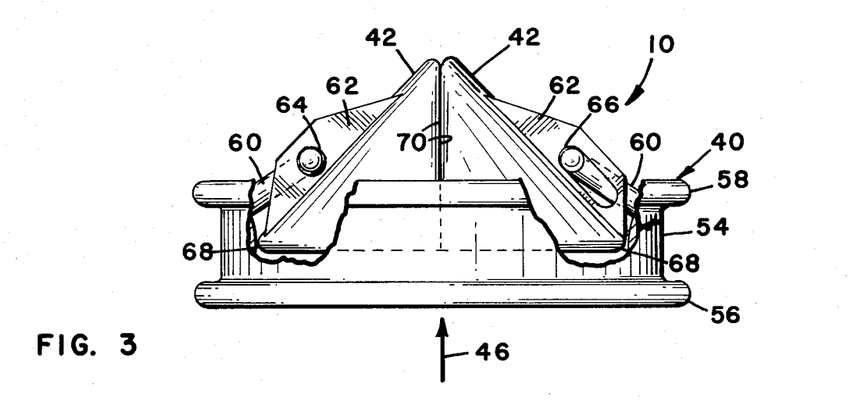
FIG. 3 is a side view (partially cut away) of the first embodiment with the leaflets in the closed position.
Figure 4:
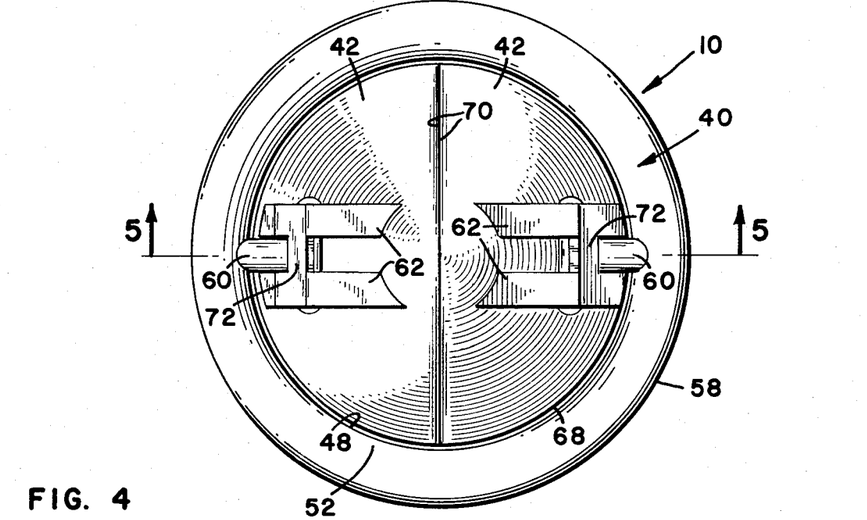
FIG. 4 is a top view of the first embodiment viewed from the outflow aspect with the leaflets in the closed position.

FIG. 2 is a perspective view of the prosthetic heart valve 10 representing a first embodiment of the invention. Valve 10 comprises a base or annular housing 40 within which a pair of semiconical leaflets 42 are supported for movement between open and closed positions. The leaflets 42 are shown in the closed position in FIG. 2. Extending around the annular housing 40 is a conventional sewing ring 44, shown in FIG. 1, by which the valve 10 can be sutured in place within the heart. For clarity, sewing ring 44 has been omitted from FIGS. 2–7. The sewing ring 44 is typical of other sewing rings that have been employed hereinbefore as intermediaries in securing prosthetic heart valves in place, and thus does not comprise a part of the invention except as used in combination therewith. As will be explained in greater detail hereinafter, leaflets 42 open and close in response to a pressure differential across the valve 10 to control the direction and passage of blood therethrough.

Figure 5:
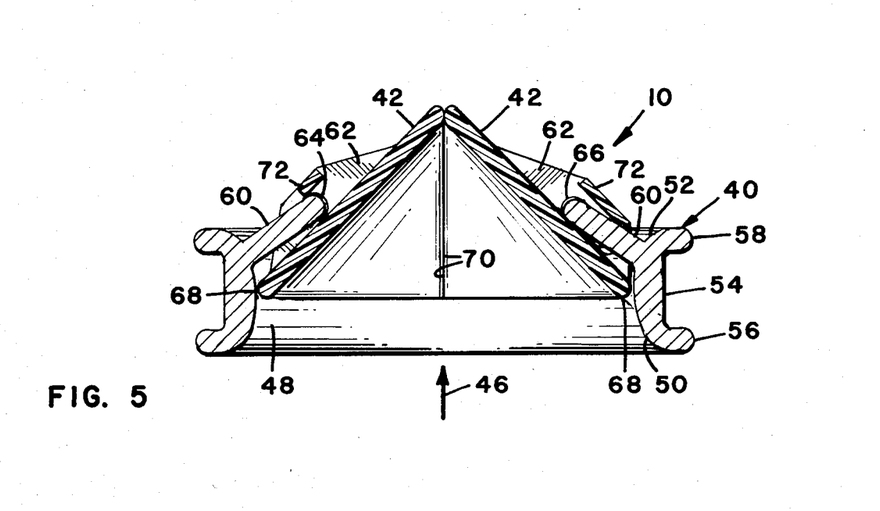
FIG. 5 is a cross sectional view taken along lines 5—5 of FIG. 4 in the direction of the arrows.
Figure 6:
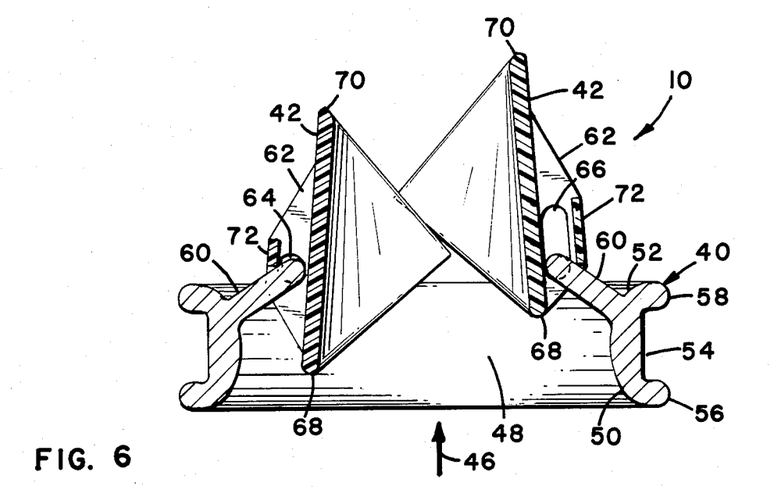
FIG. 6 is a cross sectional view similar to FIG. 5, but with the leaflets in the open position.
Figure 7:
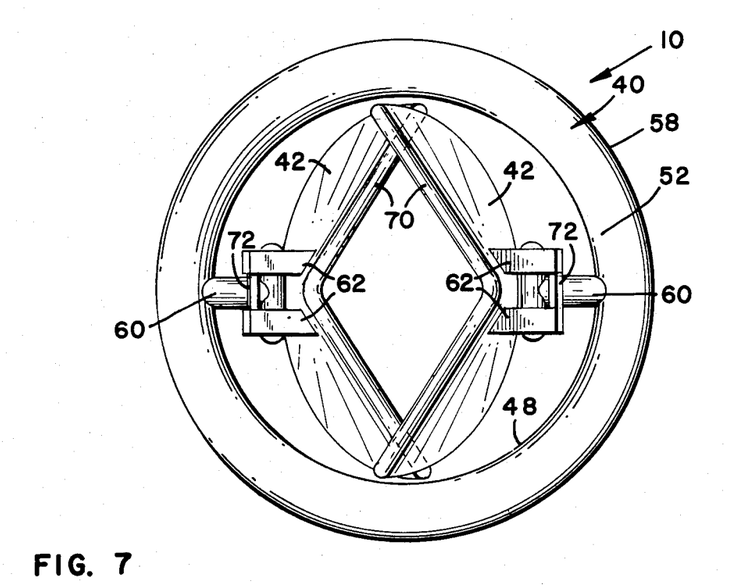
FIG. 7 is a top view of the first embodiment with the leaflets in the open position.
Figure 8:
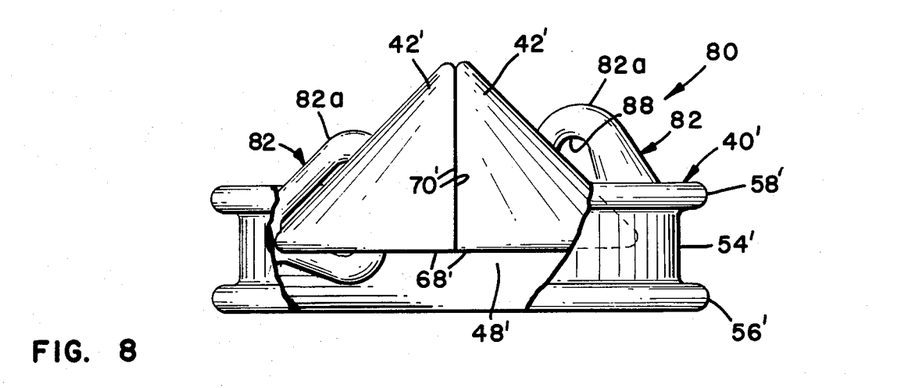
FIG. 8 is a side view (partially cut away) of the second embodiment with the leaflets in the closed position herein.
Figure 9:
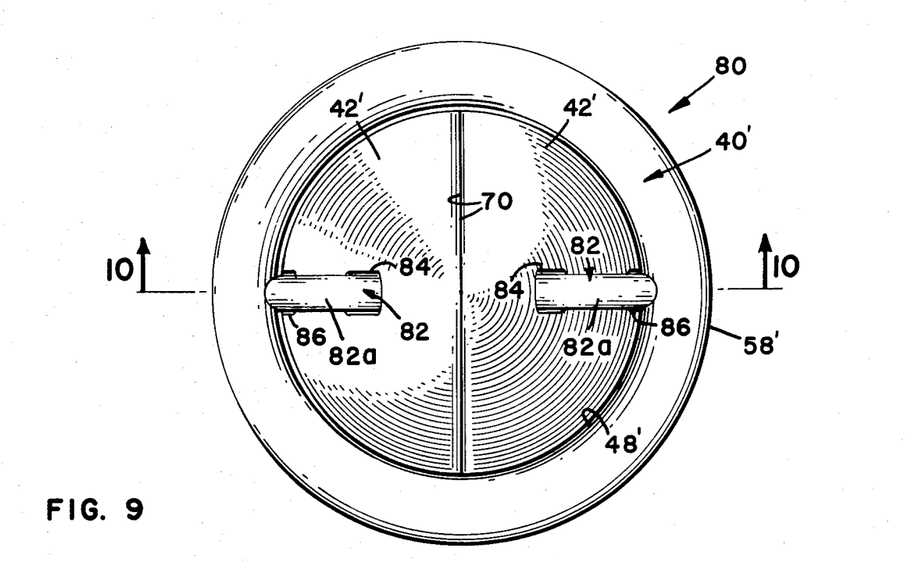
FIG. 9 is a top view of the second embodiment with the leaflets in the closed position.
Figure 10:
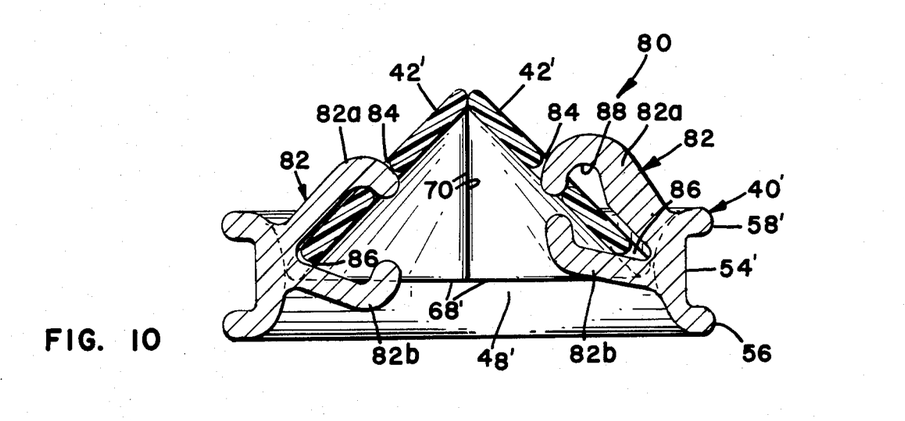
FIG. 10 is a cross sectional view taken along lines 10—10 of FIG. 9 in the direction of the arrows.

The constructional details of the prosthetic heart valve 10 are best shown in FIGS. 3–7. The sewing ring 44 has been omitted from these figures for purposes of clarity. Arrow 46 represents the direction of flow through valve 10. The valve housing 40 includes a circumferential inner wall 48 defined by a divergent bell-shaped inlet portion 50 and a divergent bell-shaped outlet portion 52, as is best seen in FIG. 5, to form a smooth circular passageway therethrough. The outer circumferential wall 54 of the valve housing 40 includes longitudinally spaced apart flanges 56 and 58 defining a circumferential groove or recess therebetween within which the sewing ring 44 would be located. The valve housing 40 can be of any suitable dimensions, depending upon the particular natural valve to be replaced. For example, the valve housing 40 can be about four to five millimeters wide with an internal or orifice diameter of about 20 millimeters and an outside diameter of about 24 millimeters between flanges 56 and 58. As for the material, valve housing 40 can be constructed of any suitable material, but is preferably formed of metal such as titanium or stainless steel.

A pair of T-shaped support arms 60 are provided on the outlet or downstream side of the valve housing 40 at diametrically opposite locations. Each arm 60 comprises a straight base or shank that is secured at one end to the inner wall 48 and which extends inwardly and away from the point of attachment in the direction of flow through the valve to a cross member at the opposite end of the arm. The free ends of arms 60 are received in notches or slots formed in pairs of brackets 62 attached to the leaflets 42, thereby constraining the leaflets for pivotal movement over a range of about 42 degrees. In particular, the free end of one arm 60 is received in elongated slots 64 formed in the brackets 62 attached to the left leaflet 42, while the free end of the other arm is received in elongated slots 66 formed in the brackets on the other leaflet. The brackets 62 are attached to the back or downstream side of leaflets 42. Slots 64 and 66 are generally parallel to the sides of leaflets 42, while the cross arms on the free ends of support arms 60 extend in a direction generally transverse to the leaflets and transverse to the longitudinal flow axis through valve 10.

The leaflets 42 of valve 10 are thus supported for both pivotal and translational movement relative to valve housing 40 by pin and slot connections. In accordance with the preferred construction, one of the slots, slot 66, is relatively more elongated than the other slot 64 for additional translation to facilitate the open/closing events.

The leaflets 42 are semiconical and are of thin walled construction. Each leaflet 42 includes a smoothly rounded lower edge 68, which edges together form a circular base disposed substantially midway between the inlet and outlet portions 50 and 52 of the inner wall 48 of housing 40. The ring-like circular base of leaflets 42 has an outside diameter which is slightly less (on the order of a fraction of a millimeter) than the inside diameter of the inner valve housing wall 48 to avoid interference therewith during movement of the leaflets. The adjoining side edges 70 of leaflets 42 can be substantially flat for closely abutting one another when the leaflets are in the closed position for sealing purposes; however, the adjoining side edges are preferably smoothly rounded as shown to facilitate opening and closing, which rounded configuration provides sufficient sealing while preventing appreciable backflow and hemolysis.

As illustrated, leaflets 42 define a circular cone having an apex located along the longitudinal flow axis and having sides angled at approximately 45 degrees. It will be understood, however, that semiconical sections of other suitable angles can be utilized and that the angles of the semiconical leaflets 42 are not critical to practice of the invention accept insofar as they relate to the height of valve 10 with respect to the generally available clearance within the heart chambers. Leaflets 42 can be constructed of any suitable material, and in the preferred embodiment are constructed of nonmetallic material such as Pyrolite-carbon material.

The artificial heart valve 10 operates as follows. Upon a pressure differential across valve housing 40 wherein the pressure on the outflow side is relatively less than that on the inflow side, such as during ventricular relaxation or diastole, leaflets 42 pivot to the open position shown in FIGS. 6 and 7. A stop 72 extending between brackets 62 on each leaflet engages the corresponding arm 60 to limit opening movement of the leaflet. As illustrated, leaflets 42 open to a maximum position wherein their sides form an angle of about 87 degrees, or slightly less than 90 degrees, with a lateral plane extending through the valve housing 40. The leaflet 42 having the larger elongated slots 66 formed in the brackets 62 thereof is allowed to translate outwardly from the valve housing 40 relatively more than the other leaflet during opening for ease of operation.

The leaflets 42 when open present minimal frontal area to blood flowing through the valve housing 40, thereby minimizing additional load and stress on the heart. Blood flows with ease centrally through valve housing 40 as well as across the leaflets 42 with minimal resistance and flow characteristics similar to a healthy natural valve.

Valve 10 closes when the pressure differential thereacross changes as blood rushes back through the valve in the opposite direction of arrow 46, which occurs during ventricular contraction or systole. Blood is trapped behind the leaflets 42, forcing them to close across the passageway in valve housing 40. The closing rate of leaflets 42 accelerates as the apex of each leaflet swings across the backflow. Leaflet 42 with the relatively smaller slots 64 in brackets 62 thereof closes first, followed by the other leaflet having the relatively longer slots 66 in the brackets thereon. Thus, the opening and closing movement of one leaflet 42 is primarily pivotal and slightly translational, while the opening and closing movement of the other leaflet is also pivotal but slightly more translational. Valve closure is complete when leaflets 42 contact each other along their side edges 70 and when their bottom edges 68 are properly recessed within the valve housing 40. Due to the clearance between the circular outer periphery of leaflets 42 and the inner wall 48 of housing 40, some residual backflow or leakage is expected, however, this is considered minimal.

FIGS. 8–12 illustrate a prosthetic heart valve 80 incorporating a second embodiment of the invention. The valve 80 incorporates numerous components that are substantially identical in construction and operation to the components of valve 10 illustrated in FIGS. 1–7. These identical components have been designated in FIGS. 8–12 with the same reference numerals utilized in the description of valve 10 hereinbefore, but are differentiated therefrom by means of a prime (') designation.

Figure 11:
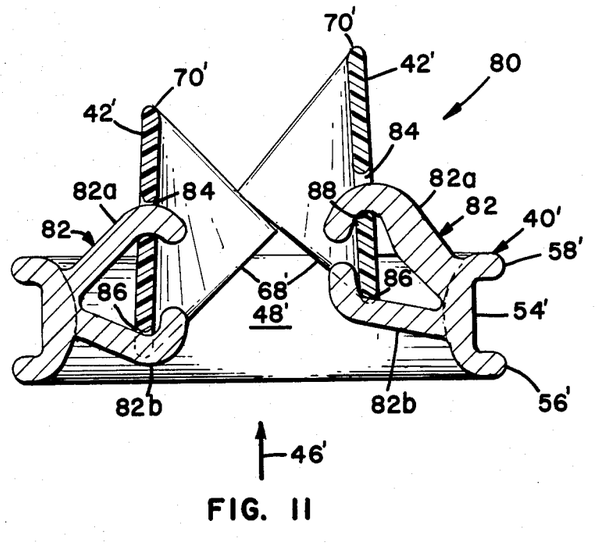
FIG. 11 is a cross sectional view similar to FIG. 10, but with the leaflets in the open position.
Figure 12:
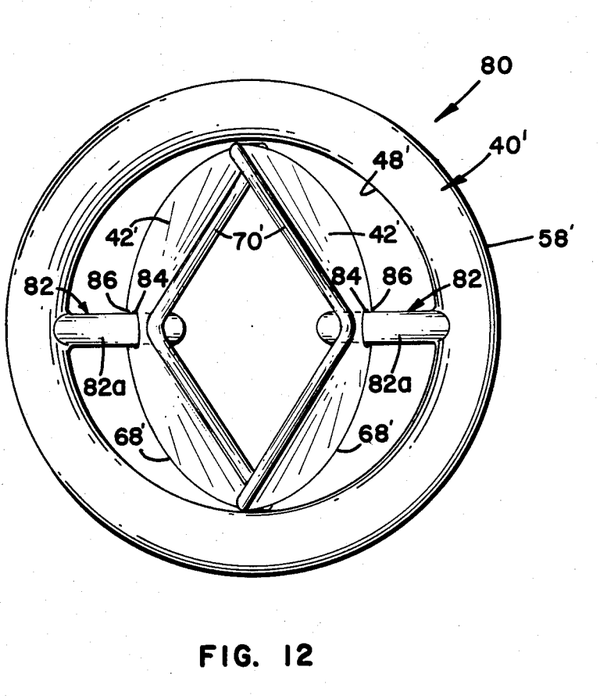
FIG. 12 is a top view of the second embodiment with the leaflets in the open position.

The primary distinction between valve 80 and valve 10 comprises the fact that leaflets 42' of valve 80 are supported by retaining/control arms 82 rather than by means of pin and slot connections as in the case of valve 10. Each retaining/control arm 82 is of generally C-shaped configuration including an upper strut 82a and a lower strut 82b. The upper strut 82a of each retaining-/control arm 82 fits into an aperture 84 formed directly through the side of the corresponding leaflet 42', while the lower strut 82b extends through a notch 86 provided in the lower edge 68' thereof. Aperture 84 and notch 86 and struts 82a and 82b are configured so that leaflets 42' are constrained and guided for primarily pivotal movement between open and closed positions. The distal ends of the lower struts 82b are turned downstream and function as open stops when leaflets 42' are in the full open position as is best seen in FIG. 11. In accordance with the preferred construction, one of the upper struts 82a includes a notch 88 near the distal end thereof, which distal end fits through an aperture 84 which is relatively more elongated than the aperture in the opposite leaflet to permit some translation of one leaflet as the leaflets move between their open and closed positions. Aside from the use of retaining/control arms 82, aperture 84 and notch 86 formed directly in the semiconical leaflets 42', valve 80 functions substantially identically to valve 10 described hereinbefore.

From the foregoing, it will thus be apparent that the present invention comprises an improved artificial heart valve having several advantages over the prior art. Both embodiments of the valve disclosed herein utilize semiconical leaflets that pivot between full open and closed positions over angles of movement smaller than those of the valves of the prior art, particularly the pivoting disc type valves. Each embodiment incorporates support means that permits pivotal and some translational movement of the leaflets, and which preferably permits relatively greater translational movement for one of the leaflets in order to facilitate operation. The heart valve herein is of compact construction and utilizes a valving member of split semiconical construction that is responsive to changes in pressure differential across the valve to control blood flow therethrough. Other advantages will be evident to those skilled in the art.

Although particular embodiments of the invention have been illustrated in the accompanying Drawing and described in the foregoing Detailed Description, it will be understood that the invention is not limited to the embodiments disclosed, but is intended to embrace any alternatives, modifications, rearrangements and/or substitutions of elements falling within the scope of the invention as defined by the following Claims.

I claim:

1. A heart valve prosthesis, comprising:
   a base having spaced apart inner and outer circumferential walls, the inner wall defining a circular passageway therethrough with an inlet and an outlet disposed on opposite sides of said base;
   the outer wall of said base including a pair of longitudinally spaced apart circumferential flanges defining a predetermined groove therebetween surrounding said base for receiving a sewing ring by which the valve can be sutured in place within a heart;
   a plurality of semiconical leaflets that together define a conical valving element with a circular lower edge disposed within the passageway in said base;
   asymetrical mounting means for supporting said leaflets on said base for pivotal and translational movement between open and closed positions in response to changes in pressure differential thereacross for flow control through the valve;
   said mounting means including an arm secured at one end to said base adjacent to each leaflet and extending away from the outlet to the other end received in a predetermined opening formed on the associated leaflet; and
   stop means associated with said asymetrical mounting means for limiting opening pivotal movement of said leaflets.

2. The heart valve of claim 1, wherein said base is formed of metallic material.

3. The heart valve of claim 1, wherein said leaflets are formed of nonmetallic material.

4. A heart valve prosthesis, comprising:
   a base having spaced apart inner and outer circumferential walls, the inner wall defining a circular passageway therethrough with an inlet and an outlet disposed on opposite sides of said base;
   a plurality of semiconical leaflets that together define a conical valving element with a circular lower edge disposed within the passageway in said base; and
   means for mounting said leaflets on said base for pivotal and translational movement between open and closed positions in response to changes in pressure differential thereacross for flow control through the valve;
   said mounting means including: a pair of spaced apart brackets attached to each leaflet with registering elongate slots extending through said brackets;
   a T-shaped arm secured at one end to said base adjacent to each leaflet with the free end of said arm being received in the slots in said brackets on the corresponding adjacent leaflet such that said leaflets are supported for pivotal and translational movement; and
   stop means associated with each leaflet for limiting opening pivotal movement thereof.

5. A heart valve prosthesis, comprising:
   a base having spaced apart inner and outer circumferential walls, the inner wall defining a circular passageway therethrough with an inlet and an outlet disposed on opposite sides of said base;
   a plurality of semiconical leaflets that together define a conical valving element with a circular lower edge disposed within the passageway in said base; and
   means for mounting said leaflets on said base for pivotal and translational movement between open and closed positions in response to changes in pressure differential thereacross for flow control through the valve;
   said mounting means including: a generally C-shaped retaining control arm fixed to said base adjacent to each leaflet;
   each retaining/control arm including an arcuate upper strut extending through an aperture formed in the corresponding leaflet and a lower strut extending through a notch formed in the lower edge of the corresponding leaflet, with the lower struts of said retaining/control arms having turned distal ends that operate as open stops for limiting opening pivotal movement of said leaflets.

6. A prosthetic heart valve, comprising:
   a base having inner and outer spaced apart circumferential walls, the inner wall defining a circular passageway therethrough with an inlet and outlet disposed on opposite sides of said base;
   the outer wall of said base including a pair of longitudinally spaced apart circumferential flanges defining a predetermined groove therebetween surrounding said base for receiving a sewing ring by which the valve can be sutured in place within a heart;
   a pair of opposing semiconical leaflets disposed at least partially within the outlet side of the passageway in said base;
   a pair of spaced apart brackets attached to each leaflet with registering slots extending through said brackets;
   a T-shaped arm secured at one end to said base adjacent to each leaflet, with the other free end of said arm being received in the slots of said brackets on the corresponding leaflet whereby said leaflets are constrained for pivotal movement between open and closed positions; and stop means associated with each T-shaped arm for limiting opening pivotal movement of said leaflets in response to changes in pressure differential across the valve.

7. The check valve of claim 6, wherein said base is formed of metallic material.

8. The check valve of claim 6, wherein said leaflets are formed of nonmetallic material.

9. The prosthetic valve of claim 6, wherein the inner wall of said base at the inlet and outlet of the passageway therethrough is bell-shaped and diverges outwardly.

10. The prosthetic valve of claim 6, wherein the slots in said brackets on at least one of said leaflets is elongated to permit predetermined translation of said leaflet(s) during opening and closing.

11. A prosthetic valve adapted for implantation in the heart to control direction of blood flow, comprising:
   a base having inner and outer spaced apart circumferential walls with the inner wall defining a circular passageway therethrough with an inlet and outlet disposed on opposite sides of said base;
   the outer wall of said base including a pair of longitudinally spaced apart circumferential flanges defining a predetermined groove therebetween surrounding said base for receiving a sewing ring by which the valve can be sutured in place within a heart;
   a pair of opposing semiconical leaflets positioned within the outlet of the passageway in said base; and
   a C-shaped retaining/control member fixed to said base adjacent to each leaflet;
   each retaining/control member including an upper arcuate strut extending through an aperture formed in the corresponding leaflet, and a lower strut extending through a notch formed in the lower edge of the same corresponding leaflet whereby said leaflets are constrained and guided for pivotal movement between open and closed positions;
   the lower arms of said retaining/control members having turned distal ends which operate as open stops to limit opening pivotal movement of said leaflets.

12. The check valve of claim 11, wherein said base is formed of metallic material.

13. The check valve of claim 11, wherein said leaflets are formed of nonmetallic material.

14. The prosthetic valve of claim 11, wherein the upper strut of at least one of said retaining/control members includes a predetermined notch therein to permit predetermined translation of said leaflet(s) during opening and closing.

* * * * *